Figure 1:
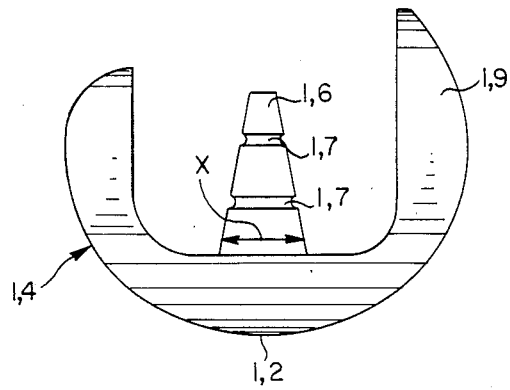

United States Patent [19]

Grobbelaar

[11] Patent Number: 4,673,408
[45] Date of Patent: Jun. 16, 1987

[54] KNEE PROSTHESIS

[75] Inventor: Charl J. Grobbelaar, Pretoria, South Africa

[73] Assignee: Arthroplasty Research & Development (Pty) Ltd., Pretoria, South Africa

[21] Appl. No.: 636,685

[22] Filed: Aug. 1, 1984

[30] Foreign Application Priority Data

Aug. 24, 1983 [ZA] South Africa .......................... 83-2059

[51] Int. Cl.$^4$ ................................................. B61F 2/38
[52] U.S. Cl. ..................................................... 623/20
[58] Field of Search ...................... 3/1, 1.9, 1.91, 1.911, 3/1.912, 1.913; 128/92 C, 92 B, 92 BC, 92 E; 623/20

[56] References Cited

U.S. PATENT DOCUMENTS 3,685,058  8/1972  Tronzo ................................. 3/1.912

FOREIGN PATENT DOCUMENTS 2906458  8/1979  Fed. Rep. of Germany ....... 3/1.911
2061730  5/1981  United Kingdom ................. 3/1.911

Primary Examiner—Richard J. Apley
Assistant Examiner—David Isabella
Attorney, Agent, or Firm—Fred Wiviott

[57] ABSTRACT

A knee prosthesis which comprises a femoral component and a tibial component, for use in a procedure involving removal of the cruciate ligaments, each component extending across the width of the joint, the femoral component presenting a pair of bearing convexities separated by a groove and curving posteriorly and upwardly for flexion, the tibial component comprising a coacting pair of bearing concavities separated by a dome, and presented as a bearing pad or pads supported on a base, the skeleto-prosthetic interface of each component presenting one or more keying element(s) adapted to penetrate the bone.

4 Claims, 10 Drawing Figures

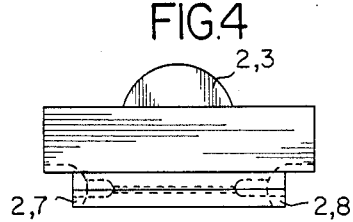
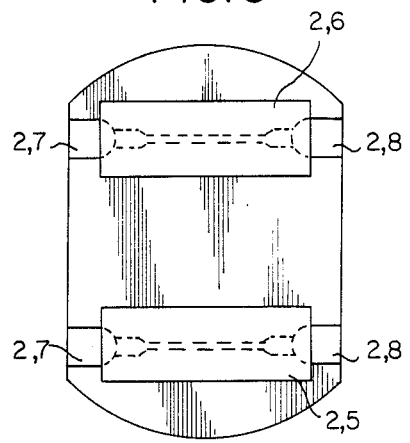
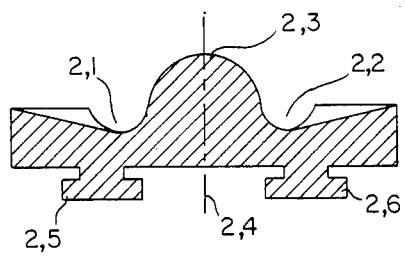

KNEE PROSTHESIS

This invention concerns improvements in and relating to knee prostheses, that is prosthetic devices for the total replacement of the knee joint.

Knee prosthetic devices are known to the applicant which are inserted in the joint after removal of diseased or damaged joint surfaces to provide two monocondylar prosthetic bearing pads one on either side of the cruciate ligaments. As a result of the large forces at work in the knee joint large prosthetic inserts led into the bone have been used to maximise the surface area available for cementing to the bone. Prosthesis loosening has, however, remained a problem. At the same time the procedure has resulted in rather extensive removal of cancellous bone with resulting diminution of salvage potential.

A knee prosthesis in accordance with this invention comprises a femoral component and a tibial component, for use in a procedure involving removal of the cruciate ligaments, each component extending across the width of the joint, the femoral component presenting a pair of bearing convexities separated by a groove and curving posteriorly and upwardly for flexion, the tibial component comprising a coacting pair of bearing concavities separated by a dome, and presented as a bearing pad or pads supported on a base, the skeleto-prosthetic interface of each component presenting one or more keying element(s) adapted to penetrate the bone.

In accordance with a preferred feature of the invention the keying elements are narrow and deep, their short dimensions extending transversely in the joint and their longer dimensions extending posteriorly and anteriorly in the joint. In this way the major surface areas of the keying elements lie in planes directed posteriorly/anteriorly and the narrow transverse dimension allows the preservation of cancellous bone in the mounting area. This provides salvage potential by a sufficient area of cancellous bone for sound bone union at the joint.

Preferably the tibial component comprises a bearing pad locked in an adjustable position on a base, the base carrying the keying elements and supporting the pad. In this arrangement the pad can be selected from materials giving particularly suitable properties as a bearing surface in coaction with the femoral component. In accordance with a preferred embodiment of the invention the pad is furthermore selected from materials which will show a suitable degree of plastic flow under compressive forces in use so as to flow into locking or gripping serrations or other formations over a period of time to enhance attachment to the base plate. For example, preferably the base has undercut keyways or grooves into which matching formations of the bearing pad can be slid so as to key the pad onto the base. Preferably there is further provision for screw insertion to lock the bearing pad in position in such keyways or grooves to provide security of placement of the pad. In addition, however, the gripping formations referred to for receiving plastic flow of the bearing pad material over a period of time will then enhance the securement of the bearing pad in the base.

In accordance with a preferred embodiment of the invention the pad and base are adapted to facilitate the relative positions of the bearing pad and base in which the former is locked or secured with respect to the latter being adjustable within a suitable range during the operative procedure. This means that the keying formations of the base can be set into the bone and final adjustment of the bearing pad with respect to the base made in situ. With this approach refinement of the positioning of the bearing pad with respect to the bone does not depend upon perfect alignment of the preparation of the bone surface or the base and the sockets in the bone for the keying elements.

Preferably the dome is provided with multilateral symmetry that is, symmetry about a vertical axis passing through the centre of the tibial component so that there is no torsional constraint on the lower limb exercised by the prosthetic device.

In accordance with a preferred embodiment of the invention the skeleto-prosthetic interfaces at least are coated with a biologically inert material preferably, for example, a ceramic. Such coating is moreover preferably provided with a coarse surface finish such as, for example, a coarse granular finish. Such a surface finish will provide a good glue bonding surface in accordance with a preferred embodiment of the invention. Nevertheless, the ceramic or other coating must be so applied to the prosthesis surfaces so as to avoid the formation of discontinuities such as may give rise to pin-hole corrosion or similar electro-chemical attack on the prosthesis. The cement will be selected so as to provide a good bond in the period commencing immediately after the operation so as to provide for quick rehabilitation of the patent.

The prosthetic components can be made from one of the super alloys which are suitable for this application such as the stainless steels or the nickel/cobalt alloys. However, where such metals are employed it is preferred that the skeleto-prosthetic interfaces of the components are coated with a biologically inert material such as a ceramic, for example a high purity alumina. In the bearing surfaces of the femoral component a very high polish is attained. By contrast in the skeleto-prosthetic interface areas a roughened finish is aimed for, for example by applying a coarse grained coating, where the inert surface makes toxic substances relatively far less detectable by the body mechanisms.

Figure 2:
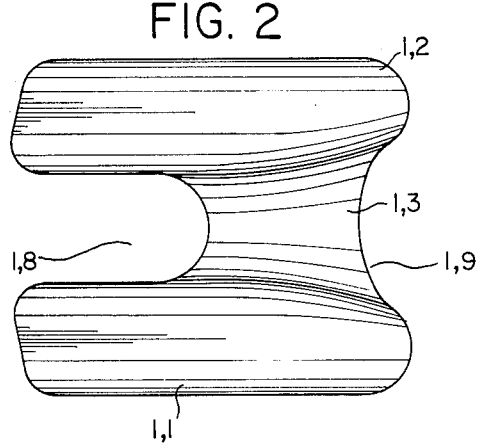
Figure 3:
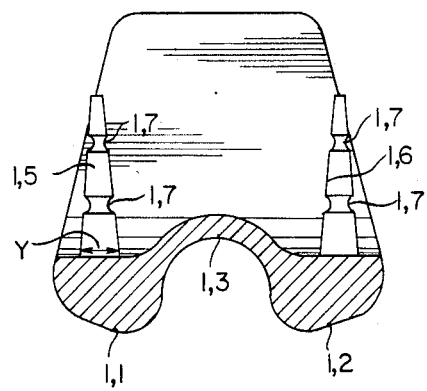
Figure 7:
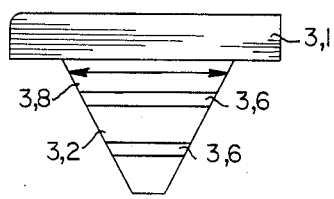
Figure 8:
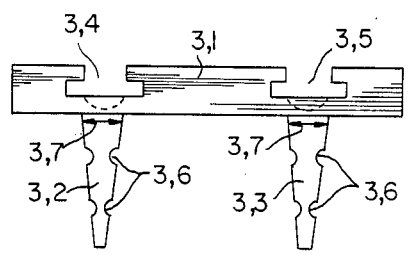
Figure 9:
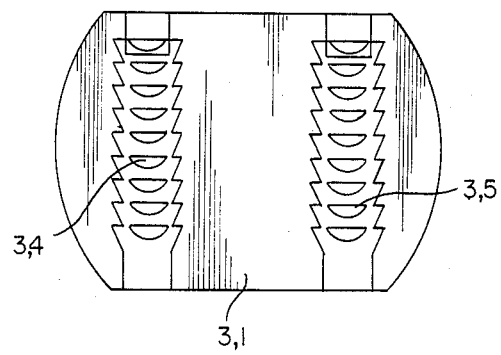
Figure 10:
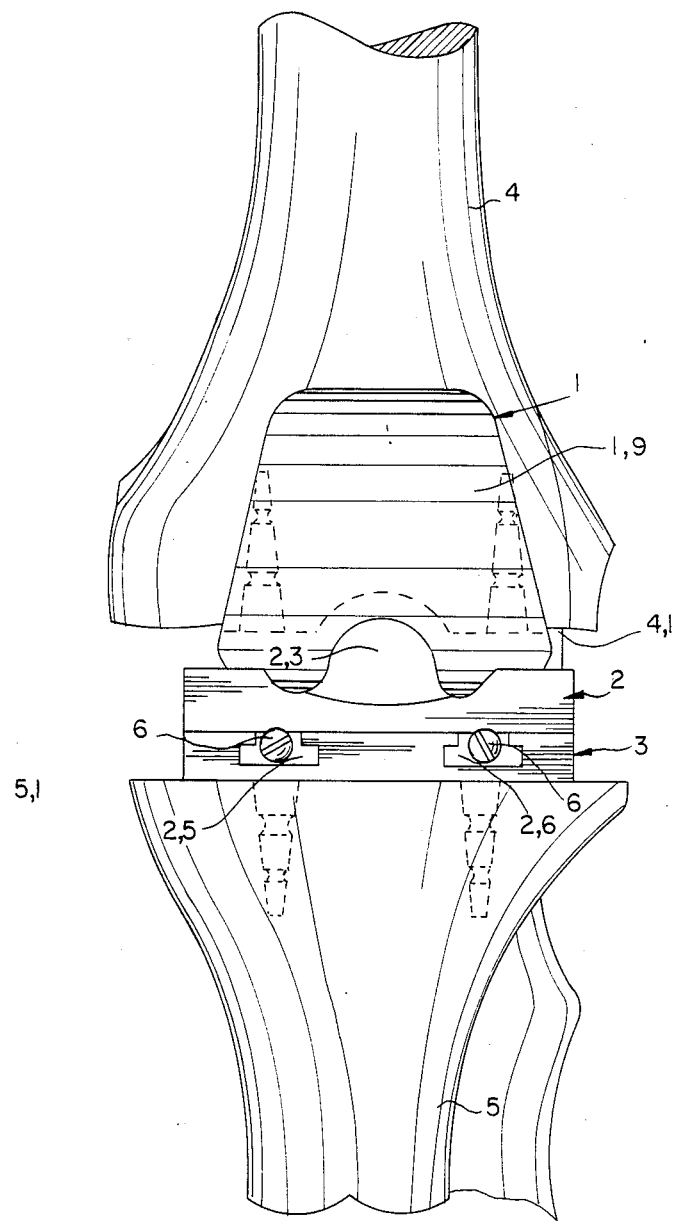

This invention will now be more fully described by way of an example with reference to the accompanying drawings, in which:

FIG. 1 is a side elevation of the femoral component of a knee prosthesis in accordance with the preferred embodiment of the invention, FIG. 2 is a plan view of the component shown in FIG. 1 turned upside down, FIG. 3 is cross sectional elevation on section A—A shown in FIG. 1, FIG. 4 is a side elevation of the tibial bearing pad, also called the tibial plateau component of the prosthesis, FIG. 5 is a plan view of a component shown in figure 4 turned upside down, FIG. 6 is a cross sectional elevation on section A—A shown in FIG. 4, FIG. 7 is a side elevation of the base plate also called the tibial wedge of the component shown in FIGS. 4 to 6, FIG. 8 is a front elevation of the base plate or tibial wedge, FIG. 9 is a plan view of the base, and FIG. 10 is a front elevation showing the prosthesis implanted in a knee joint, (showing bones only).

As shown in FIGS. 1 to 3 the femoral component comprises a fabrication in 316L stainless steel, the sliding surfaces of the component presenting a pair of condylar bearing convexities 1,1 and 1,2 separated by a groove 1,3. The convexities and the groove extend from the anterior side A to the posterior side P of the component and curve posteriorly and upwardly in the region 1,4 for flexion of the joint. A pair of keying elements 1,5 and 1,6 are provided in this example of wedge shape but with transverse grooves 1,7 for keying into holes which are provided for them in the bone during the operative procedure in the use of the cement. The posterior portion 1,4 has the groove 1,3 removed into an opening 1,8 which separates the two bearing convexities in the posterior region. The bearing convexities have surfaces 1,2 in the regions as shown which, in transverse, vertical planes parallel to section A—A as in the view of FIG. 3 are flat, and which are inclined to the horizontal at an angle greater than 0° and less than 30°, in this example of 15°. These flat surfaces extend round into the posterior region 1,4. The anterior portion 1,9 presents a high polished and somewhat hollowed surface which leads into the groove 1,3 as a bearing surface for the patella. The keying elements 1,5 and 1,6 have a larger dimension X in the anterior/posterior direction and are comparatively narrow having the dimension Y in the transverse direction, providing a minimum destruction of cancellous bone to accommodate the keying elements.

The tibial component of the prosthesis is provided in two parts, the H.D.P.E bearing pad or tibial plateau, shown in FIGS. 4 to 6 and the base plate or tibial wedge shown in FIGS. 7 to 9. The tibial plateau comprises high density polyethelene or an ultra high molecular weight polyethelene. This or another plastic is selected to provide good frictional characteristics, good wear characteristics and the right degree of plastic flow over a period of time into gripping formations of the tibial wedge which will be described below in relation to FIG. 9. Varying sizes are provided for selection and use according to the patient, for example, three sizes to enable correct ligament tensions being attained. The part provides a pair of condylar bearing concavities 2,1 and 2,2 shaped and dimensioned to coact well with the convexities 1,1 and 1,2 of the femoral component and separated by a dome 2,3 which has multilateral symmetry about a vertical axis 2,4 and the concavities 2,1 and 2,2 also have this symmetry at least to a limited extent so as to provide no torsional constraints during normal leg movements. The undersurface of the part has two T-shaped locking elements 2,5 and 2,6 running from anterior side A to posterior side P of the part. The locking elements 2,5 and 2,6 have screw holes 2,7 at the anterior side and 2,8 at the posterior side for receipt of self-tapping type screws for locking the tibial plateau into position on the tibial wedge during the operative procedure.

As shown in FIGS. 7 to 9 the tibial wedge which is made of 316L stainless steel and sand blasted, comprises a base portion 3,1 and two keying elements 3,2 and 3,3. The base 3,1 has two T-shaped or undercut grooves 3,4 and 3,5 and both grooves have teeth-like gripping formations as can be seen in the view of FIG. 9. The undercut grooves 3,4 and 3,5 are dimensioned to permit the T-shaped elements 2,5 and 2,6 of the tibial plateau to be slid into the grooves thereby locking the H.D.P tibial plateau shown in FIGS. 4 to 6 in the tibial wedge shown in figues 7 to 9. Under the compressive stresses generated in use as a bearing pad the tibial plateau is subject to plastic flow over a period of time and the material of it enters into the serrations of the teeth-like gripping formations in the tibial wedge thereby ensuring after a period of use a permanent bond between the two components. Experiments have shown that the bond is very secure to the extent that it could only be separated by destruction of the tibial plateau. The keying elements 3,2 and 3,3 are again provided with grooves 3,6 which are oriented in a horizontal direction and serve to key the elements in position in the bone when they are cemented onto the bone. As mentioned the keying elements 3, and 3,3 have a relatively narrow dimension 3,7 in the transverse direction so as to minimize the area of cancellous bone which is removed to provide sockets for these elements. In the anterior/posterior direction the dimension 3,8 of the elements is comparatively large to provide a large surface for bonding with bone.

The prosthesis is shown inserted in a knee joint in the view of FIG. 10, the femur 4 receiving the femoral prosthesis 1 and the tibia 5 receiving the tibial prosthesis which is made up of the HDP tibial plateau 2 and the tibial wedge 3. Screws 6 are shown screwed into the T-shaped anchoring elements 2,5 and 2,6 of the tibial plateau 2 so as to lock it in a suitable position in the grooves of the tibial wedge 3. In the operative procedure the cruciate ligaments are removed and a platform 5,1 is formed on the tibia 5 and a platform 4,1 on the femur 4, removing the sliding surfaces of the natural joint. Sockets are then bored in the bone to receive the keying elements 1,5, 1,6 and 3,2 and 3,3. The patella, the capsular ligaments and the collateral ligaments are retained. The dome 2,3 permits free rotation of tibia with respect to the femur. In this manner stress to the ligaments is avoided nor are tortional loads applied to the prosthesis which would otherwise constitute an influence tending to the loosening of the prosthesis in the bone. The thickness of the bearing pad 2 can be selected from a range in which the pads are preferably provided as a kit in accordance with this invention to facilitate attaining an ideal extension in particular of the capsular ligaments. As an example the thickness T as shown in FIG. 6 may be as follows:

small 2,5 mm
medium 5 mm
large 7,5 mm

The procedure employing these prostheses requires no more than a two centimetre gap to be opened up at the joint, much less than usual and this is intentionally attained with a view to minimising loss of cancellous bone. This feature, together with the narrow sockets referred to above gives salvage potential by means of bony union should the prosthetic joint fail or be contraindicated for some reason. Nevertheless good fixation is attained by virtue of the features of the prosthesis as described above.

The prosthetic devices are, as stated, preferably provided coated with an inert material so far as the active substances of the body are concerned, for example, in particular a high purity alumina ceramic is preferred. At the skeleto-prosthetic interfaces preferably a coarse finish is obtained, for example, by the use of coarse granular ceramic. The ceramic may be applied for example by high velocity high temperature detonation methods such as so-called detination coating with a view to attaining melting of the micro surface of the metal as the ceramic grains impinge on the metal thereby permitting an intimate metal-ceramic bond to be developed. Preparation of the metal surface with a view to achieving a good bond is desirable. These prostheses can be used with conventional cement such, for example, as methyl methacrylate. The ceramic coating is most important in the skeleto-interfaces but solid, cast ceramic insets can also be provided with advantage on the bearing or sliding surfaces of the femoral prosthesis as a high density, fine grain, high purity alumina ceramic surface which is given a very high polish. The extreme hardness of this material provides minimum wear and an extended life-time of the prosthesis and with the result minimum detritus resulting from which, moreover, is comparatively inert to body fluids and therefore less likely to provide toxic effects in the body. The bearing or sliding surfaces of the high density or ultra high molecular weight polyethelene tibial plateau 2 can thus slide either on stainless steel surfaces or high purity alumina ceramic surfaces, in both cases highly polished.

Apart from the wedge thickness selection which is available, anterior or posterior adjustment of the position of the pad 2 with respect to the base plate 3 is permitted by the construction and the screws 6 are used to secure the pad in the selected position.

I claim:

1. A knee prosthesis which comprises a femoral component and a tibial component, for use in a procedure involving removal of the cruciate ligaments, each component extending across the width of the joint, the femoral component presenting a pair of bearing convexities separated by a groove and curving posteriorly and upwardly for flexion, the tibial component comprising a coacting pair of bearing concavities separated by a dome, and presented as a bearing pad or pads supported on a base, the skeleto-prosthetic interface of each component presenting one or more keying element(s) adapted to penetrate the bone, said femoral component having a posterior portion, a groove formed in the posterior portion and intersecting an opening which separates the two bearing convexities in the posterior portion, the bearing convexities each having surfaces which, in transverse vertical planes are flat and inclined to the horizontal at an angle of between 0° and 30° and in which the anterior portion presents a high polished and somewhat hollowed surface which leads into the groove as a bearing surface for the patella, said keying elements being narrow and deep with their short dimensions extending transversely in the joint and their longer dimensions extending posteriorly and anteriorly in the joint, said tibial component comprising a bearing pad locked in an adjustable position on a base, the base carrying the keying elements and supporting the pad, the base having undercut keyways or grooves into which matching formations of the bearing pad can be slid so as to key the pad onto the base, and including screw means engaging said bearing pad and said base to lock the bearing pad in position in such keyways or grooves to provide security of placement of the pad.

2. A knee prosthesis as claimed in claim 1, in which the dome is provided with multilateral symmetry about a vertical axis passing through the centre of the tibial component.

3. A knee prosthesis as claimed in claim 1, in which the skeleto-prosthetic interfaces are coated with a biologically inert material.

4. The knee prosthesis set forth in claim 1 and including interlocking means formed in one of said keyways or grooves and said matching formations to inhibit relative movement there-between.

* * * * *